United States Patent [19]

Rodriguez et al.

[11] Patent Number: 5,660,828

[45] Date of Patent: Aug. 26, 1997

[54] METHOD OF TREATING AUTOIMMUNE AND/OR VIRAL-INDUCED DISEASES THAT ARE MEDIATED BY CD8 PHENOTYPE T CELLS

[75] Inventors: Moses Rodriguez, Rochester, Minn.; Subramaniam Sriram, Burlington, Vt.

[73] Assignees: Mayo Foundation for Medical Education & Research, Rochester, Minn.; University of Vermont and State Agricultural College, Burlington, Vt.

[21] Appl. No.: 177,806

[22] Filed: Jan. 6, 1994

Related U.S. Application Data

[63] Continuation of Ser. No. 863,492, Mar. 30, 1992, which is a continuation of Ser. No. 162,781, Mar. 2, 1988.

[51] Int. Cl.$^6$ .................. A61K 39/395; A61K 45/05; C07K 1/00; C07K 14/00
[52] U.S. Cl. .................. 424/154.1; 424/85.1; 530/350
[58] Field of Search .................. 424/85.8, 154.1, 424/85.1; 530/387, 350

[56] References Cited

U.S. PATENT DOCUMENTS 4,695,459  9/1987  Steinman et al. .................. 424/95

OTHER PUBLICATIONS

Rodriguez, et al., 1987, "Treatment of TMEV Induced Demyelination . . . " Neurology 37:344, Abstract #10.

Sarmiento, et al., 1980, "IgG or IgM Monoclonal Antibodies . . . " J. Immunol. 125: 2665–2672.

Rodriguez, et al., 1986, "Susceptibility to Theiler's Virus-Induced . . . " J. Exp. Med. 163: 620–631.

Huber, et al., 1984, "In Vitro Culture of Coxsackievirus Group B . . . " Infect. and Imm. 43(2): 567–573.

Rodriguez, et al, 1986, "Partial Suppression of . . . " Neurology 36: 964–970.

Friedman, et al, 1987, "Monoclonal Anti–I–A Antibody . . . " J. Virol. 61(3): 898–903.

Sriram, et al, 1986, "Treatment of Established . . . " J. Immunol. 136(12): 4464–4469.

Clatch, et al., 1985, "Theiler's Murine Encephalomyelitis Virus . . . ," Journal of Immunology vol. 135(2): 1408–1414.

*Primary Examiner*—Lynette F. Smith
*Attorney, Agent, or Firm*—Hamilton, Brook, Smith & Reynolds, P.C.

[57] ABSTRACT

A method to block cytolytic activity of CD8 phenotype T cells using an effective amount of a complement-fixing anti CD8 antibody is described. The anti CD8 antibody may be used to treat patients with immunopathologic disorders induced by viruses or (autoimmune diseases) such as multiple sclerosis, viral or post-viral polyneuropathy, viral or post-viral myocarditis, insulitis, encephalomyelitis, myositis, synovitus, and arthritis.

9 Claims, 4 Drawing Sheets

FIG.2A
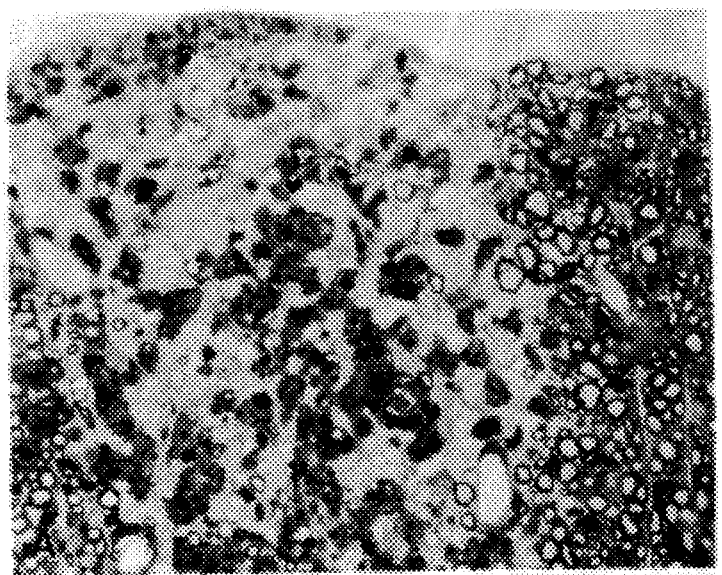
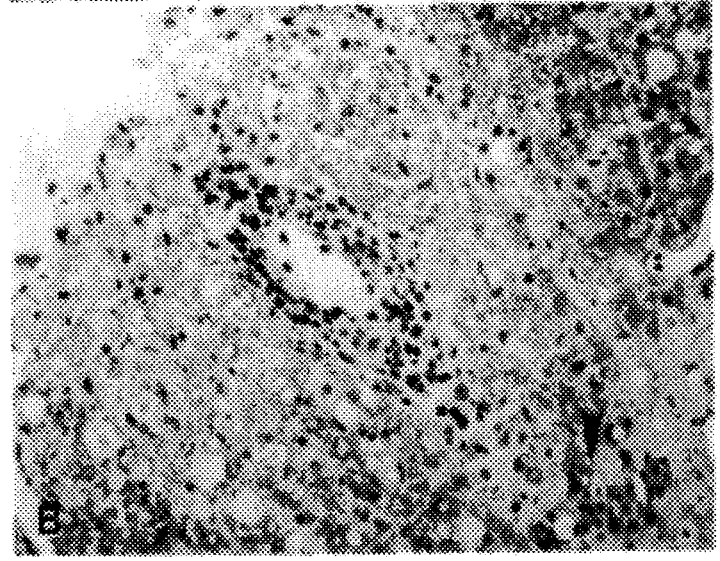
FIG.2B

FIG.3A
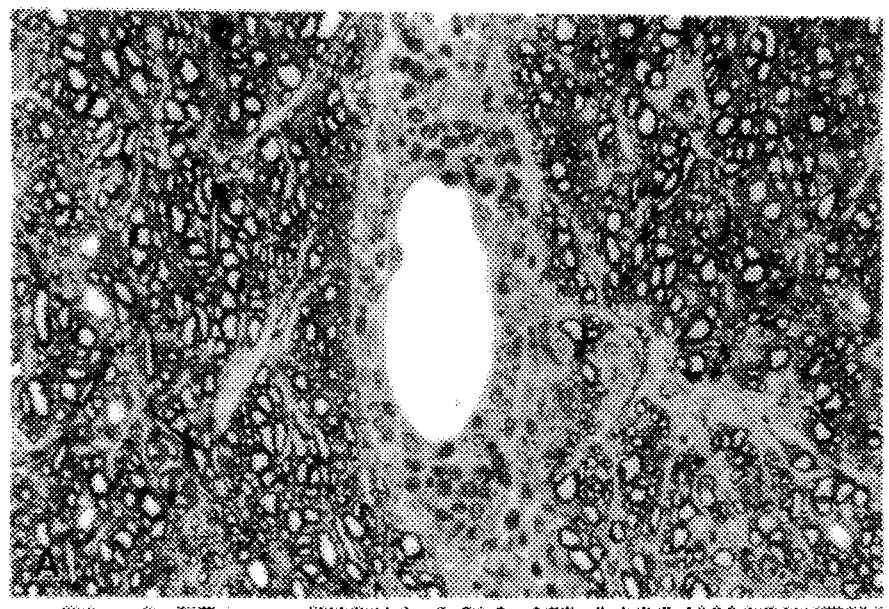
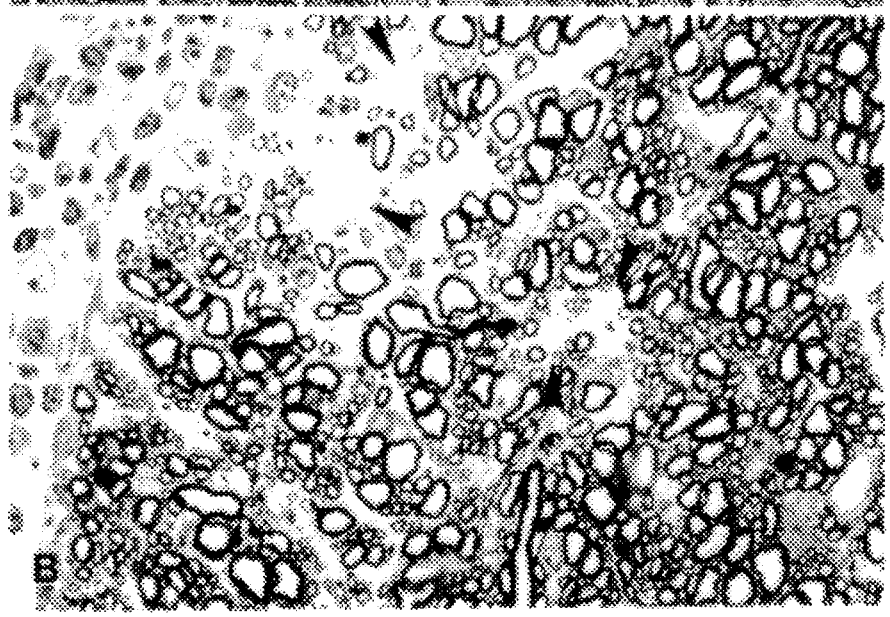
FIG.3B

5,660,828

METHOD OF TREATING AUTOIMMUNE AND/OR VIRAL-INDUCED DISEASES THAT ARE MEDIATED BY CD8 PHENOTYPE T CELLS

This is a continuation of application Ser. No. 07/863,492 filed on Mar. 30, 1992, now abandoned, which is a continuation of application Ser. No. 07/162,781, filed on Mar. 2, 1988, now abandoned.

This invention was made with Government support under Grant Number NS00849 and K07-9500920 awarded by the National Institutes of Health. The Government has certain rights in this invention.

TECHNICAL FIELD

This invention relates to a method for treating immunopathologic disorders induced by viruses or autoimmune diseases that are mediated by CD8 phenotype T cells using anti-CD8 antibody.

BACKGROUND

The role of immunologic mechanisms in autoimmune disorders and virus has been the focus of increasing interest and investigation. Among the autoimmune disorders that have been studied are multiple sclerosis, systemic lupus erythematosus, rheumatoid arthritis, polymyositis, myasthenia gravis, Sjogren's disease and hemolytic anemias.

Certain autoimmune diseases affect primarily the nervous system. Autoimmune diseases of this type include the demyelinating diseases such as multiple sclerosis, (central nervous system) and acute idiopathic polyneuritis (Guillian-Barre' Syndrome) (peripheral nervous system).

Multiple sclerosis is a chronic relapsing disease which affects many areas of the central nervous system white matter. A major feature of multiple sclerosis is inflammatory demyelination in the central nervous system with lesions primarily in the periventricular areas of the cerebrum, cerebellum, brain stem and spinal cord. Common manifestations of multiple sclerosis are motor weakness, paresthesias, impairment of visual acuity and diplopia.

To better understand human demyelinating diseases, such as multiple sclerosis, viral diseases of the central nervous system of mice, such as Theiler's murine encephalomyelitis virus (TMEV), have been studied. TMEV is a picornavirus, which induces an unusual biphasic neurologic disease of the central nervous system in susceptible mice (M. Theiler, Science, 80: 122 (1934); H. L. Lipton, Infect. Immuno., 11: 1147 (1975)). The disease produced by Theiler's "original" (TO) strain of virus [H. L. Lipton and M. C. Dal Canto, Ann. Neurol., 6: 25 (1979)] is characterized by acute neuronal polioencephalitis followed by chronic primary demyelination with persistence of virus in glial cells (M. Rodriguez et al., Ann. Neurol., 13: 426 (1983)). Infection with tissue culture-adapted strains of TMEV results in prominent myelin destruction but minimal polioencephalitis, even though neurons produce vital antigens during the acute phase.

It has been suggested that the chronic demyelination induced by TMEV is mediated by immune cells. The pathologic features are strikingly similar to those of experimental autoimmune encephalomyelitis (EAE) with lymphocytes present in a perivascular distribution in the brain and spinal cord (M. C. Dal Canto and H. L. Lipton, Lab. Invest., 33: 626 (1975)). Furthermore, immunosuppression with cyclophosphamide [H. L. Lipton and M. C. Dal Canto, Science, 192: 62 (1976); H. L. Lipton and M. C. Dal Canto, Infect. Immun., 15: 903 (1977)], antitymphocyte serum [R. P. Roos et al., J. Neuroimmunol., 2: 223 (1982)], cyclosporin A [M. Rodriguez and J. Quddus, J. Neuroimmunol., 13: 159 (1986)], or monoclonal antibody to immune-response gene products [M. Rodriguez et al., Neurology, 36: 964 (1986); Friedmann et al., J. Virol., 61: 898 (1987)] partially suppresses demyelination.

Demyelination may result as an immune response directed against persistently infected oligodendrocytes (myelin-producing cells) (Rodriguez et al., Immunol. Today, 7: 359 (1986)). As a consequence of viral infection, antigens not associated with normal oligodendrocytes would appear on the cell surface and be recognized by T cells in association with MHC glycoproteins. Accordingly, there is a need to provide a method for blocking cytolytic activity of T cells which recognize cell surface antigens not associated with normal (non-virus) infected cells; thereby, providing a method to suppress inflammation and demyelination in patients suffering from autoimmune diseases affecting the central nervous system.

SUMMARY OF THE INVENTION

The present invention provides a method for treating immunopathologic disorders induced by viruses or autoimmune diseases that are mediated by CD8 phenotype T cells. The method involves administering to a patient a therapeutically effective amount of an anti-CD8 antibody that is cytotoxic or interferes with the function of CD8 phenotype T cells of the patient. In accordance with the method of the present invention, the anti-CD8 antibody effectively blocks the cytolytic activity of the CD8 phenotype T cells.

While a polyclonal antibody can be used in the present invention, in a preferred embodiment the antibody employed is a Class IgG1 or IgG2 monoclonal antibody. Preferably, the association constant of the antibody is at least $10^7$ L/ml. Also, in a preferred embodiment, the antibody is administered in amounts ranging from about 10 to about 100 mg.

Other features and advantages of the invention will be apparent from the following detailed description and appended claims.

BRIEF DESCRIPTION OF THE FIGURES

FIG. 2 shows spinal cord white matter of SJL/J mice (ARALDITE-embedded sections stained with toluidine blue).

FIG. 3 shows spinal cords of SJL/J mice of mice treated with mAb 2.43 (anti-Lyt2) in accordance with protocols I and III.

DETAILED DESCRIPTION OF THE INVENTION

Figure 1:
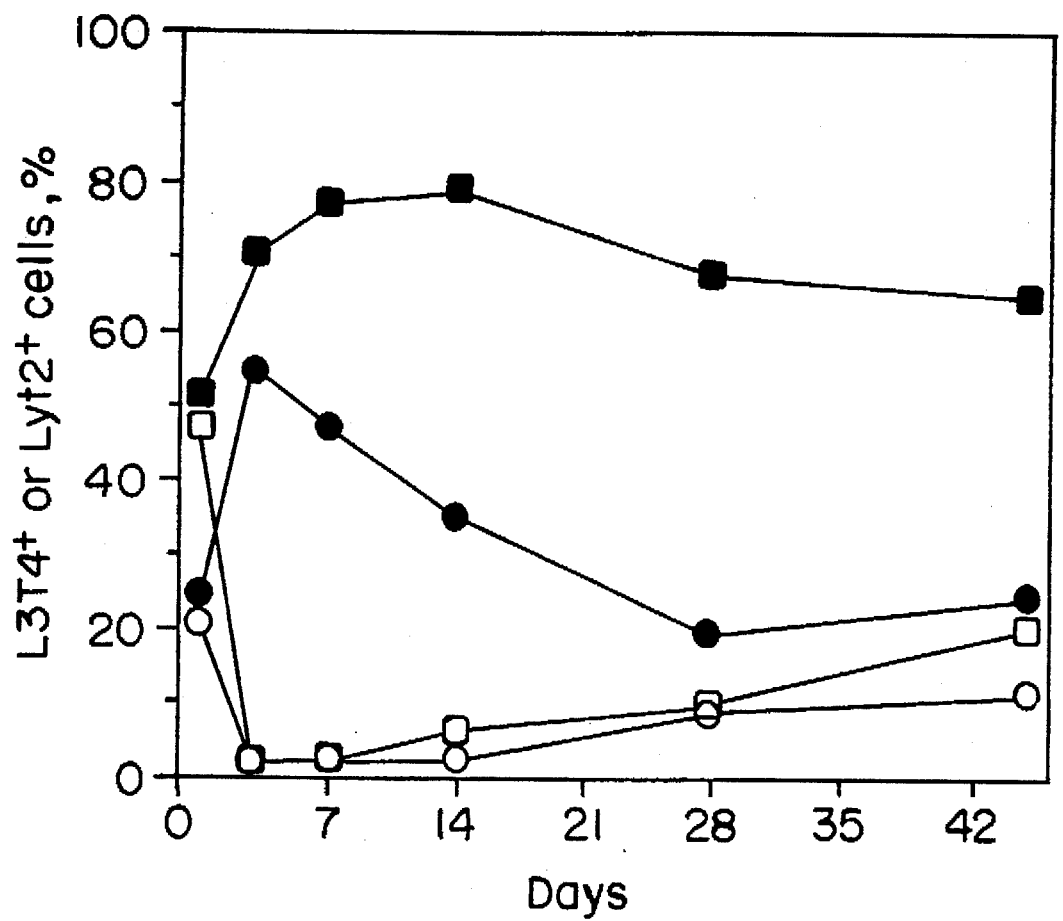
FIG. 1 is a graphic representation of percentage of T lymphocytes (by flow cytometry) in lymph node cells from SJL/J mice given 1 mg (i.p.) of mAb GK1.5 (L3T4) or 2.43 (Lyt 2).

The term "CD8" as used herein in connection with human therapy denotes a particular class I-restricted membrane antigen that is restricted to human cytotoxic/suppressor T cells. This antigen is described in Meyer S. C., et al., Proc. Natl. Acad. Sci. USA, 79: 4395 (1982). The term "CD8" is also used herein to denote homologous T cell membrane antigens that occur in other species.

The present invention is directed to preventing or alleviating immunopathologic disorders induced by viruses or autoimmune diseases that are mediated by CD8 phenotype T cells using anti-CD8 antibody. In the context of the invention, the terms "treat" and "therapy" and the like refer to prophylaxis or attenuation of existing disease.

Membrane antigens that characterize T cell subsets are believed to be highly conserved between mammalian species. Therefore, homologs of CD8 exist in other mammalian species and treatment of virus and autoimmune induced diseases in mammals other than humans can be achieved by administering antibody homologous to CD8 for other species.

Treatment of virally mediated autoimmune diseases according to the present invention is mediated by the CD8 phenotype T cells by administering an effective amount of complement-fixing cytotoxic anti-CD8 antibody to a patient with tissue injury resulting from the patient's own immune response to the virus. The beneficial effect of such immunotherapy can be shown in two animal models of demyelinating diseases, TMEV and encephalomyocarditis (EMC) virus, in susceptible strains of mice. Although the development of immune response to virus is generally beneficial, development of immune response to virus-infected cells can destroy these cells serving vital physiologic function. For example, adult mice infected with lymphocytic choriomeningitis virus (LCMV) die although LCMV is a relatively noncytopathic virus. Cerebral damage and death results from LCMV specific T cytotoxic cells attacking LCMV infected cells in the brain. T cells of the CD8 phenotype are known to produce this pathological state. Oldstone, et al., *Nature,* 321: 239–243 (1986).

The present invention is directed to depleting the critical CD8 positive T lymphocyte from the body using anti CD8 antibody and leaving the rest of the immune response, such as "helper function", antibody production, complement system, intact; thereby, diminishing the cellular injury to critical physiological tissue.

Immunopathologic disorders that may be treated by the method of the present invention are those mediated by CD8 phenotype T cells. Among the diseases for which the present invention can be used are multiple sclerosis, rheumotoid arthritis, systemic lupus erythematosus, Sjogren's disease, polymyositis, ulcerative colitis and myasthemia gravis. The present invention is preferably directed to treatment of demyelinating diseases such as multiple sclerosis.

While the anti-CD8 antibody employed in the present invention can be a purified polyclonal antibody, a monoclonal antibody is preferred. At present, monoclonal antibodies employed are of mouse origin because of the availability of rodent tumor fusion partners for hybridization. However, the present invention envisions use of human anti-human CD8 antibody or a chimeric antibody that is "half mouse" and "half human".

Monoclonal antibodies useful in the present invention can be obtained using techniques well known and described in the literature. (Kohler and Milstein, *Nature,* 256: 495–497 (1975)). Tumor cell lines, reagents, and conditions used in this procedure have also been previously described. (Somatic Cell Genetics, 5: 957–972 (1979); Monoclonal Antibodies ((1980) Plenum Press)). To produce anti-CD8 producing hybridomas, suitable host animals, such as mice or rabbits are immunized with human peripheral blood lymphocytes or T cell-enriched human peripheral blood lymphocytes.

The anti-CD8 antibody used in the present invention should be capable of fixing human complement and be highly cytotoxic to the target CD8 positive T cells in the presence of complement. While the immunoglobulin class of the antibody is not believed to be critical, it will normally be an IgG1 or IgG2 with an association constant of at least about $10^7$ L/mol., usually between from about $10^7$ to about $10^8$ L/mol.

Patient treatment using the method of the present invention involves administering therapeutic amounts of the CD8 antibody. The antibody may be formulated with conventional pharmaceutically acceptable parenteral vehicles for administration by injection. These vehicles comprise substances which are essentially nontoxic and nontherapeutic such as water, saline, Ringer's solution, dextrose solution, Hank's solution or the like. It is to be understood that antibody formulations may also include small amounts of adjuvants such as buffers and preservatives to maintain isotonicity, physiological pH and stability. Preferably, the antibody is formulated in purified form substantially free of aggregates and other protein at concentrations ranging from about 0.1 to about 10 mg/ml.

As indicated by the above formulation, the antibody may be administered parenterally. Typically, the antibody will be delivered intravenously, as a bolus. The antibody can also be administered to a patient on a periodic or continuous basis.

The dose of the antibody formulation to be administered will depend upon the patient and the patient's medical history. However, the dose should be sufficient to deplete a substantial portion, usually more than about 90%, of the CD8 positive T cell population of the patient. Dosages for adult humans envisioned by the present invention and considered to be therapeutically effective will range from between about 10 and 100 mg. However, it is to be understood that doses can readily be adjusted to provide appropriate amounts of the antibody to children.

The invention will be further described by reference to the following detailed examples.

Suppression of Demyelination Disease by Monoclonal Antibody 2.43 Treatment

To study the role of T cells in the development of chronic demyelination, we have examined the effect of in vivo depletion with monoclonal antibodies (mAbs) to two T-cell subsets (L3T4$^+$ and Lyt2$^+$) (D. P. Dialynas et al., *J. Immunol.,* 131: 2445 (1983); M. A. Sarmiento, *J. Immunol.,* 125: 2665 (1980). L3T4 and Lyt2 antigens are produced in a mutually exclusive manner and are analogous to human CD4 (class II-restricted) and CD8 (class I-restricted) T-cell antigens, respectively. As shown below, in vivo, mAb to Lyt2.2 antigen (mAb 2.43) is effective in suppressing demyelination when administered at the time of virus inoculation or 15 days after infection with virus. In contrast, depletion of class II-restricted T cells by giving anti-L3T4 antibody (mAb GK1.5) at the time of virus inoculation results in worsening of demyelination, encephalitis, and death; no effect was seen when this mAb was given to mice with established demyelinating disease.

Antibodies

Cells of hybridomas GK1.5 and 2.43, both of which synthesize rat antibody of the IgG2b isotype, were obtained from the American Type Culture Collection (ATCC). The ATCC deposit number for mAbs 2.43 is TIB210. GK1.5 and 2.43 recognize monomorphic determinants on L3T4 and Lyt2.2 molecules, respectively (D. P. Dialynus et al., supra.; M. A. Sarmiento, supra.). Monoclonal antibodies obtained from ascites fluid were used for in vivo therapy and for staining cells in flow cytometry. To prepare ascites fluid, $1 \times 10^7$ hybridoma cells were injected into BALB/c mice that had been primed with 2,6,10,14-tetramethylpentadecane and irradiated sublethally with 500 rad. Ascites fluid containing the mAb was obtained on day 7 and purified by affinity chromatography as described by S. Sriram and C. A. Roberts, *J. Immunol.*, 136: 4464 (1986), the disclosure of which is incorporated by reference herein. In addition to these mAbs, culture supernatants from cell lines 30-H12 (anti-Thy1.2) and 53-7.313 (anti-Lyt1) were used for flow cytometry. See J. A. Ledbetter and L. A. Herzenberg, *Immunol. Rev.* 47: 63 (1979).

Flow Cytometry

Two hundred microliters of a suspension of washed cells from lymph node, spleen, thymus, or peripheral blood ($5 \times 10^6$/ml) was incubated on ice for 20 minutes with an equal volume of a 1:500 dilution of purified ascites fluid or hybridoma culture supernatant containing anti-Thy1, anti-Lyt1, anti-Lyt2, or anti-L3T4 mAbs. After washing, the cells were stained with a 1:150 dilution of goat anti-rat Kappa chain IgG conjugated to FITC (Becton Dickinson, Mountain View, Calif.) which does not cross-react with mouse Igs. After incubation on ice for another 30 minutes, the cells were washed twice and analyzed on the cytofluorograph (Ortho Diagnostic Systems, Inc., Raritan, N.J.). To evaluate the degree of background staining, lymphocytes were stained with the second antibody (goat anti-rat Kappa chain IgG conjugated to FITC) alone.

Virus

The origin of the tissue culture-adapted DA strain of TMEV used for these experiments has been described (Rodriguez et al., *Ann. Neurol.*; 13:426 (1983)). Virus was assayed by the plaque method on L2 cells by established protocols without modification. The protocols are described in Rodriguez et al., *Ann. Neurol.*; 13: 426 (1983), incorporated by reference herein.

Animals and Experimental Protocol

SJL/J ($H-2^s$) female mice (4 to 6 weeks of age) from The Jackson Laboratory (Bar Harbor, Me.) were inoculated intracerebrally with $2 \times 10^5$ PFUs of TMEV in 10 ul of vehicle. The mice were treated with 1 or 2 mg of mAb, 0.5 ml of normal rat serum, or 0.5 ml of isotype control Ig2b in three different protocols.

Protocol I. mAb or serum was given i.p. on days −1, 0, and +1 (day 0 was time of virus infection).

Protocol II. mAb was given on days 9, 10, and 11 (a time immediately preceding the onset of demyelination in the spinal cord) and then continued at two injections per week.

Protocol III. mAb was given on days 15, 16, and 17 (a time at which inflammation is prominent in the spinal cord and there is minimal but definite demyelination); these mice also were given $1 \times 10^9$ sheep RBCs i.p. on day 28 (7 days prior to sacrifice, on day 35) to determine if mAb therapy had suppressed the humoral immune response to an irrelevant antigen.

The mice were perfused with Trump's fixative and the spinal cords were processed to provide 1-um-thick ARALDITE-embedded sections and 2-um-thick glycol methacrylate-embedded sections. A detailed morphologic analysis was performed on each of 25 coronal spinal cord sections from each animal, producing analyses of 2,350 sections. A pathologic score based on inflammation and demyelination was obtained for each animal as described by M. Rodriguez and J. Quddus, *J. Neuroimmunol.*, 13: 159 (1986); Rodriguez et al., *Neurology*, 36: 964 (1986), each incorporated by reference herein. The maximum pathologic score, 100, indicates the presence of inflammation or demyelination or both in every quadrant of all 25 spinal cord sections of one mouse.

Antibody Titers Agsint TMEV

Anti-TMEV antibodies were measured by ELISA with DA antigen purified in a cesium chloride gradient in the manner described by Rodriguez et al, *Neurology*. 36: 964 (1986).

Sheep RBC Agglutination Assay

Serum'samples from treated mice were assayed for IgM hemagglutination of sheep RBCs in the manner described by Rodriguez et al., *Neurology*, 36: 964 (1986).

Statistical Analysis

The Wilcoxon rank-sum test for two samples was used to evaluate statistical significance of differences in pathologic scores between groups of mice that received various mAbs or control serum.

Kinetics of T-Cell Subset Depletion with mAbs GK1.5 and 2.43

As shown in FIG. 1, a single injection, 1 mg i.p., of either mAb GK1.5 or mAb 2.43 resulted in greater than 95% depletion of L3T4$^+$ or Lyt2$^+$ cells, respectively, from the lymph nodes. This depletion occurred rapidly and reached a nadir at 3 days at which time no staining above background levels was detected with anti-L3T4 or anti-Lyt2 when the animal had received mAb GK1.5 or 2.43, respectively. Repopulation of depleted cells occurred gradually over the following 5 to 6 weeks. At all time points examined, the thymocytes remained unaffected but depletion was seen in spleen and peripheral blood. The background staining of lymphocytes was less than 5%, indicating minimal nonspecific binding of rat Igs on the surface of lymphocytes. These experiments showed that in vivo therapy with rat mAbs GK1.5 and 2.43 results in long-lasting depletion of the appropriate T-cell subset and involved all lymphoid organs except thymus. Pathologic analysis of spinal cord sections was performed on day 35 after infection; at this time the lymphocyte subsets remained depleted. Other anti-Lyt2 antibodies with IgM isotype failed to deplete lymphocytes and did not affect the pathologic features of TMEV-induced demyelination.

Pathologic Observations

In Vivo Treatment With mAb GK1.5 (anti-L3T4)

Death after virus infection according to protocol I occurred at day 17 in two mice, day 20 in two, day 21 in two, day 25 in one, and day 26 in one; the remaining eight mice survived for 35 days but showed profound hind-limb paralysis. As seen in Table I below the pathologic score in mice surviving to time of sacrifice was significantly higher ($P<0.05$) than that in mice receiving normal rat serum.

TABLE I

Pathologic Scores in Mice with TMEV-Induced Demyelination: Effect of Treatment with mAbs to T-Lymphocyte Subsets

| | | | Pathologic score on day 35 | | | |
|---|---|---|---|---|---|---|
| | | | Meningeal Inflammation | | White Matter Inflammation and Demyelination | |
| mAb | Protocol | n | Mean ± SE | P* | Mean ± SE | P* |
| GK1.5 (anti-L3T4)† | I | 7 | 51.9 ± 4.3 | <0.01 | 51.0 ± 3.9 | <0.01 |
| | II | 19 | 30.2 ± 5.2 | NS | 24.4 ± 6.0 | NS |
| | III | 4 | 29.5 ± 9.8 | NS | 26.7 ± 9.1 | NS |

TABLE I-continued

Pathologic Scores in Mice with TMEV-Induced
Demyelination: Effect of Treatment with mAbs
to T-Lymphocyte Subsets

| | | | Pathologic score on day 35 | | | |
|---|---|---|---|---|---|---|
| | | | Meningeal Inflammation | | White Matter Inflammation and Demyelination | |
| mAb | Pro-tocol | n | Mean ± SE | P* | Mean ± SE | P* |
| 2.43 (anti-Lyt2)†† | I | 10 | 19.6 ± 5.3 | <0.05 | 22.7 ± 5.8 | 0.02 |
| | III | 20 | 18.7 ± 3.0 | <0.05 | 19.7 ± 3.4 | <0.05 |
| Normal rat serum | I | 18 | 30.2 ± 10.3 | | 28.1 ± 10.2 | |
| | II | 5 | 27.9 ± 2.9 | | 27.2 ± 4.5 | |
| | III | 5 | 29.7 ± 9.7 | | 28.1 ± 9.7 | |
| Ig2b (isotype control) | III | 6 | 34.2 ± 4.5 | | 31.4 ± 4.9 | |

*By Wilcoxon rank-sum test, for difference from control serum treatment regimen.
†Five of 12 TMEV-infected animals died prior to sacrifice (day 35).
††Development of host antibody response to mAb precluded long-term treatment (protocol II), in contrast to treatment with mAb GK1.5.

As seen in FIG. 2, there were extensive inflammatory infiltrates in the meninges and white matter as well as multiple demyelinated axons in almost every spinal cord section examined. More specifically, FIG. 2A shows a large area of primary demyelination in mouse treated with normal rat serum. Multiple inflammatory cells and macrophages in intimate association with demyelinated axons can be seen. Relatively normal myelin is apparent at the edges of this photograph. (x450). In FIG. 2B, Intense inflammatory infiltrate surrounding a blood vessel in mouse treated with mAb GK1.5 (anti-L3T4) by protocol I is seen. The majority of the white matter shows myelin destruction with intramyelin vacuoles. Inflammation also extends into the gray matter (arrowhead). (x280.) Inflammatory cells were in direct contact with axons undergoing demyelination. Random pathologic analysis of animals dying prior to day 35 revealed extensive demyelination as well as inflammation within the gray matter of the spinal cord. In contrast, there were no deaths in animals treated with mAb GK1.5 on days 9, 10, and 11 (protocol II) or on days 15, 16, and 17 (protocol III). The extent of demyelination gradually decreased as the mAb GK1.5 treatment was begun later after virus infection. There was a trend for animals treated with mAb GK1.5 on days 9, 10, and 11 to show less demyelination than controls but the numbers did not reach statistical significance.

In Vivo Treatment with mAb 2.43 (anti-Lyt2)

SJL/J mice receiving mAb 2.43 consistently showed less meningeal inflammation and demyelination in the spinal cord (Table I). No animals treated with this mAb showed paralysis. The beneficial effect was seen irrespective of whether the treatment was begun early (at the time of virus infection) or after the onset of demyelinating disease. However, the greatest effect was seen with animals treated on days 15, 16, and 17 (protocol III). The spinal cords of these mice were characterized by inflammatory cells surrounding blood vessels, but the extent of demyelination was less than in controls as seen in FIG. 3. FIG. 3A illustrates the observed inflammatory infiltrate surrounding blood vessel in mouse treated with mAb 2.43 (anti-Lyt2) (protocol I). Despite the inflammation, the majority of myelin sheaths appear normal. (x450.) FIG. 3B illustrates evidence of single axons undergoing primary demyelination (arrowheads) in mouse treated with mAb 2.43 (protocol III). Many spinal cord sections from mice treated with mAb 2.43 failed to show abnormalities. (x700.)

The majority of spinal cord sections showed no demyelinating lesions in animals treated with mAb 2.43. However, no animal was completely free of disease despite almost complete depletion of the Lyt2$^+$ subset of T lymphocytes. Some demyelination was present, suggesting that the virus itself has the ability to induce demyelination without an accessory class I-restricted T-cell response.

Virus Titers

There was no difference observed in mean virus titers in brain and spinal cord of mice surviving until sacrifice as indicated in Table II below. Because three of the four mice treated with mAb GK1.5 by protocol I died prior to day 35, it is not possible from this analysis to determine if mice dying early had higher virus titers in their central nervous system. However, mice dying early after mAb GK1.5 treatment had prominent polioencephalomyelitis, indicating increased viral replication within neurons.

TABLE II

Viral Titers in Central Nervous System of
SJL/J Mice Treated With mAbs to T-Lymphocyte Subsets

| mAb or antiserum | Protocol | n | Mean virus titer, $\log_{10}$* |
|---|---|---|---|
| 2.43 | I | 3 | 4.38 |
| GK1.5 | I | 1† | 4.11 |
| 2.43 | III | 4 | 3.58 |
| GK1.5 | III | 4 | 3.96 |
| NRS | I | 4 | 4.25 |

*Values are expresssed as PFUs on L2 cells per gram of tissue (brain and spinal cord). Limit of the assay was 50 PFU/g.
†Three of four mice died prior to sacrifice (day 35).

Antibody Titers (by ELISA) Against Purified DA Antigen

Figure 4:
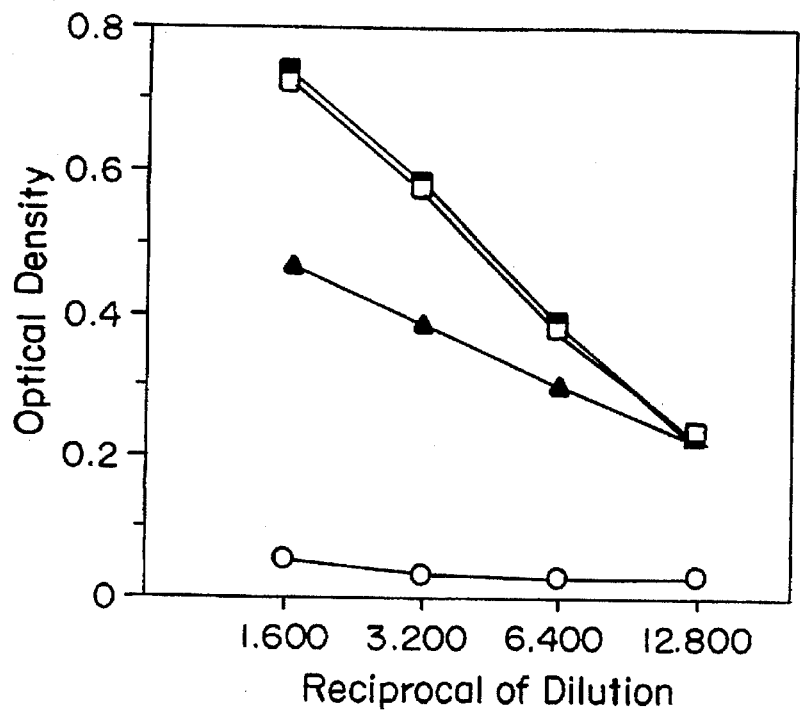
FIGS. 4 and 5 are graphic representations of titers of IgG to purified TMEV antigen measured by ELISA. Values shown are means from 5 to 10 mice in each group.
Figure 5:
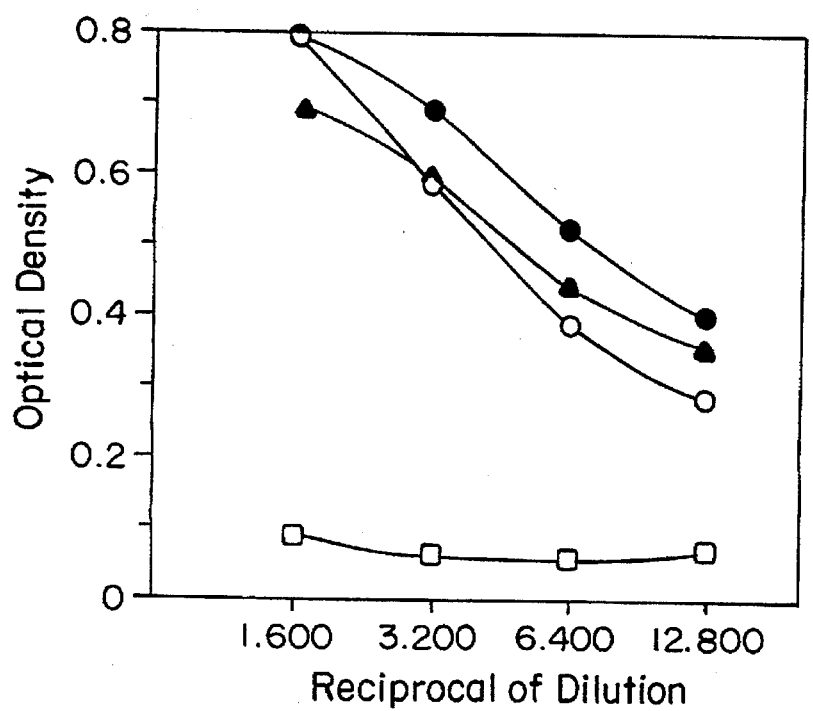

At sacrifice, all mice had high anti-TMEV titers in the serum, irrespective of mAb treatment, compared with controls (See FIG. 4). There was a tendency for anti-TMEV titers to be lower in infected mice treated with mAb GK1.5 (protocol III) compared with mice treated with normal rat serum or mAb GK1.5 (protocol I). TMEV-infected mice treated with mAb 2.43 (protocol III) had slightly higher titers than corresponding controls. However, this difference did not reach statistical significance, suggesting that this difference in antibody titer was not biologically relevant.

Agglutination of Sheep RBCs in Mice Treated with mAb to T-Cell Subsets

Mice treated with mAb GK1.5 (protocol III) had no detectable agglutination titer to sheep RBCs on day 35, indicating profound immunosuppression in regard to this irrelevant antigen (Table III). In contrast, all other mice treated with either mAb 2.43 or normal rat serum showed high agglutination titers. The highest titers were seen in mice treated with mAb 2.43 (protocol III), suggesting a possible decrease of a suppressor T-cell subset by the mAb. This suggested that treatment with mAb 2.43 inhibited demyelination without causing profound immunosuppression to an irrelevant antigen (i.e. sheep red blood cells).

TABLE III

Antibody Response to Sheep RBCs in Mice Infected with TMEV and Treated With mAbs to T-Lymphocyte Subsets

| mAb or antiserums | Protocol | Agglutination titer (IgM), $\log_2$* |
|---|---|---|
| GK1.5 | III | Not dectected |
| 2.43 | III | 10.52 ± 0.83 |
| Normal rat serum | III | 6.98 ± 1.10 |

*Mean ± SE.

As described above the effects of therapy with mAbs to T-cell subsets indicate that in mice with TMEV-induced demyelination mAb GK1.5 (directed at class II-restricted T cells) and mAb 2.43 (directed at class I-restricted T cells) depleted the appropriate subset of T cells in lymph nodes, spleens, and peripheral blood for 6 to 8 weeks after a single i.p. injection of 1 mg of purified mAb. Early treatment with mAb GK1.5 (days −1, 0, and +1 relative to virus injection) resulted in death, encephalitis, and increased demyelination in the majority of animals tested. Treatment with mAb 2.43 resulted in less meningeal inflammation and fewer demyelinating lesions in the spinal cord, irrespective of whether the mAb was given early or after demyelinating disease was established (days 15, 16, 17). Beneficial response to mAb therapy did not correlate with titers of virus isolated from the central nervous system or serum. These results indicate that class II-restricted T cells have an important role during early disease in preventing overwhelming encephalitis; and that class I-restricted T cells are believed to be critical effector cells during chronic demyelinating disease.

What is claimed is:

1. A method of treating a mammal for an immunopathologic disorder, the disorder or the disease mediated by CDS+ phenotype T cells, comprising:
    administering to the mammal a therapeutically effective amount of an anti CD8 antibody that is cytotoxic to or inhibits the function of said T cells of said mammal, thereby blocking cytolytic activity of the CDS+ phenotype T cells.

2. The method of claim 1 wherein said mammal is a human.

3. The method of claim 2 wherein the disease is selected from the group consisting of: multiple sclerosis, Guillain-Barre syndrome, systemic lupus erythematosus, rheumatoid arthritis, Sjogren's disease, polymyositis, vasculitis, ulcerative colitis, and myasthenia gravis.

4. The method of claim 2 wherein the disorder is demyelination.

5. The method of claim 1 wherein said amount of antibody is in the range of from about 10 to about 100 mg.

6. The method of claim 1 wherein the immunopathologic disorder is induced by a virus and the anti CD8 antibody is cytotoxic to cells infected by the virus.

7. The method of claim 1 wherein the anti CD8 antibody is mAb 2.43.

8. The method of claim 1, wherein the antibody is a Class IgG1 monoclonal antibody or a Class IgG2 monoclonal antibody.

9. A method of reducing demyelination of the spinal cord in a mammal, comprising administering to the mammal an anti-CD8 antibody which is cytotoxic to or inhibits the function of CD8+ phenotype T cells of the mammal, thereby reducing demyelination of the spinal cord.

* * * * *

UNITED STATES PATENT AND TRADEMARK OFFICE
CERTIFICATE OF CORRECTION

PATENT NO. : 5,660,828
DATED : August 26, 1997
INVENTOR(S) : Moses Rodriguez and Subramaniam Sriram It is certified that error appears in the above-identified patent and that said Letters Patent is hereby corrected as shown below:

```
Claim 1, line 3:  delete "CDS+" and insert --CD8*--.
Claim 1, line 8:  delete "CDS+" and insert --CD8*--.
```

Signed and Sealed this

Twenty-third Day of December, 1997

Attest:

BRUCE LEHMAN

Attesting Officer

Commissioner of Patents and Trademarks